United States Patent [19]

Zingle et al.

[11] Patent Number: 5,497,942
[45] Date of Patent: Mar. 12, 1996

[54] DISPERSANT DELIVERY SYSTEM AND METHOD FOR PRODUCING AND USING SAME

[75] Inventors: Ralph D. Zingle, Elkton, Md.; Mary W. Tilley, Middletown; William L. Mead, Wilmington, both of Del.

[73] Assignee: W. L. Gore & Associates, Inc., Newark, Del.

[21] Appl. No.: 185,092

[22] Filed: Jan. 21, 1994

[51] Int. Cl.[6] .................................................. A61L 9/04
[52] U.S. Cl. .................................. 239/6; 239/53; 428/905
[58] Field of Search ........................... 239/6, 34, 53–56, 239/60; 428/905

[56] References Cited

U.S. PATENT DOCUMENTS

| | | | |
|---|---|---|---|
| Re. 32,513 | 10/1987 | Seaber et al. | 239/6 |
| 1,129,897 | 3/1915 | Owen | 239/45 |
| 1,944,375 | 1/1934 | Schneider | 239/42 |
| 2,219,959 | 10/1940 | Laidley | 239/43 |
| 2,443,139 | 6/1948 | Krause | 239/43 |
| 2,766,069 | 10/1956 | Tennyson | 239/43 |
| 3,169,705 | 2/1965 | Geiger | 239/43 |
| 3,727,840 | 4/1973 | Nigro | 239/43 |
| 3,790,081 | 2/1974 | Thornton et al. | 239/55 |
| 3,951,622 | 4/1976 | Wilk | 239/6 |
| 4,114,284 | 9/1978 | Weber et al. | 239/56 X |
| 4,248,380 | 2/1981 | Lee et al. | 239/6 |
| 4,356,969 | 11/1982 | Obermayer et al. | 239/6 |
| 4,387,849 | 6/1983 | Van Loveren et al. | 239/6 |
| 4,413,779 | 11/1983 | Santoni | 239/45 |
| 4,445,641 | 5/1984 | Baker et al. | 239/6 |
| 4,605,165 | 8/1986 | Van Loveren et al. | 239/6 |
| 4,614,299 | 9/1986 | Van Loveren et al. | 239/6 |
| 4,753,389 | 6/1988 | Davis | 239/6 |
| 4,793,555 | 12/1988 | Lee et al. | 239/6 |
| 4,824,827 | 4/1989 | Kelly et al. | 422/119 X |
| 4,889,286 | 12/1989 | Spector | 239/47 |
| 4,898,328 | 2/1990 | Fox et al. | 239/6 |
| 4,915,301 | 4/1990 | Munteanu | 239/45 |
| 4,917,301 | 4/1990 | Munteanu | 239/43 |
| 4,923,119 | 5/1990 | Yamamoto et al. | 239/55 |
| 4,948,047 | 8/1990 | Zembrodt | 239/34 |
| 5,165,964 | 11/1992 | Imai | 427/245 |
| 5,230,867 | 7/1993 | Kunze et al. | 239/53 X |
| 5,235,863 | 8/1993 | Bailey et al. | 73/863.23 |

FOREIGN PATENT DOCUMENTS

| | | | |
|---|---|---|---|
| 749979 | 10/1970 | Belgium | 239/60 |
| 2254844 | 2/1990 | Japan . | |
| 5320255 | 12/1993 | Japan . | |
| 8807383 | 10/1988 | WIPO . | |
| 9211924 | 7/1992 | WIPO . | |
| 9405480 | 3/1994 | WIPO . | |

*Primary Examiner*—Andres Kashnikow
*Assistant Examiner*—Lesley D. Morris
*Attorney, Agent, or Firm*—David J. Johns

[57] ABSTRACT

An improved apparatus and method for the delivery of various dispersants to a surrounding environment is disclosed. The apparatus comprises a composite membrane which is resistant to wetting by low surface tension dispersant emitting substances and provides an essentially uniform rate of release of dispersant into the environment. Previous problems of inconsistent dispersant release and apparatus leakage are avoided and a more durable, compact, and reliable dispersant delivery system is provided.

22 Claims, 3 Drawing Sheets

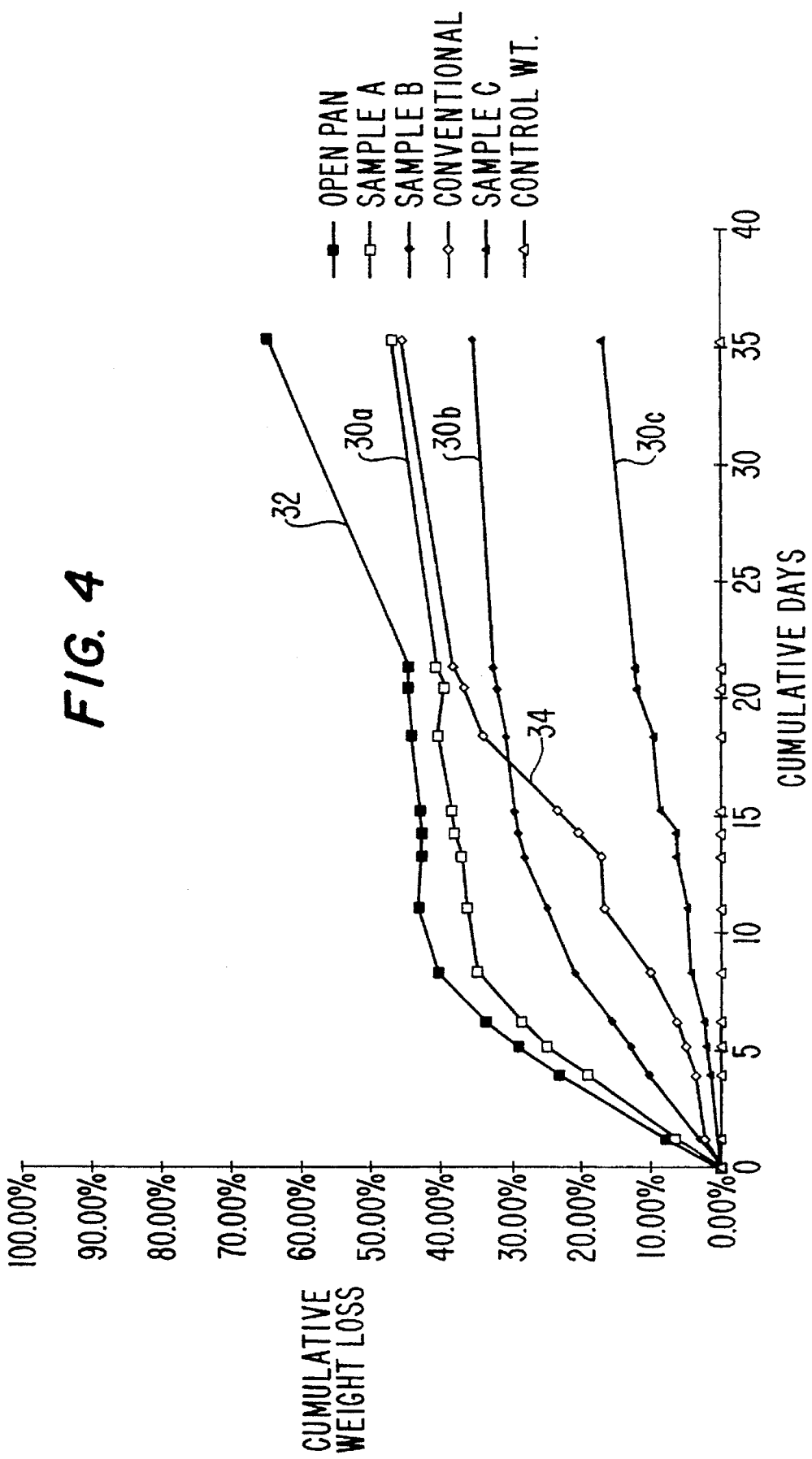

5,497,942

DISPERSANT DELIVERY SYSTEM AND METHOD FOR PRODUCING AND USING SAME

BACKGROUND OF THE INVENTION

1. Field of the Invention

The present invention relates to methods and apparatus for the delivery of fragrances, perfumes, deodorizers, pest repellents, and other dispersants to surrounding environment.

2. Description of Related Art

Delivery of various dispersants to surrounding environments is an area of continuing interest. This procedure usually employs a solid, liquid, or gaseous dispersant which is placed into a gaseous or particulate form and delivered periodically or continuously to surrounding air. Of particular interest is the continuous delivery of dispersant from a stationary receptacle over an extended period of time. Among the dispersants commonly delivered in this manner are various scents of perfumes and similar fragrances, deodorizers, pesticides and pest repellents, corrosion inhibitors, moisturizers, desiccates, medicinal vapors, scented oils, "neat" oils (i.e., straight oil without admixture or dilution), etc. Examples of apparatus providing this function are illustrated in U.S. Pat. Nos. 1,129,897 issued Mar. 2, 1915 to Owen, Jr. (air moisturizer), 2,219,959 issued Oct. 29, 1940, to Laidley (container humidifier), 2,766,069 issued Oct. 9, 1956 to Tennyson (apparatus delivering corrosion inhibitor vapors), 3,169,705 issued Feb. 16, 1965 to Geiger (device for continuous emission of active substances), and 3,727,840 issued Apr. 17, 1973, to Nigro (dispersant container and dispenser).

A major problem with the delivery of certain dispersants over an extended period of time, particularly highly volatile chemicals such as "neat" oils, spiced oils, and oily/concentrated fragrances for deodorizing, is achieving a uniform delivery of the dispersant. All too often the rate of dispersant delivery begins excessively and then drops steadily or rapidly to an inadequate amount. This condition is due in part to the volatile nature of some dispersants which dispense their most volatile elements immediately and release less volatile elements at much slower rates. Additionally, if dispersion is through a wick or similar device, there is a tendency for residues to build-up in the wick and decrease its effectiveness over time at transferring dispersant. This condition can also lead to poor quality of fragrance and/or a change in the fragrance "note" (i.e., original scent) over time.

The inconsistent release of chemical dispersants is viewed as unacceptable in numerous respects. First, immediate release of excessive odor can be objectionable and, depending upon the dispersants employed, may be hazardous. Second, the operational life of the dispersant delivery system is severely restrained, both due to an initial waste of dispersant which eliminates its availability for long-term use and to limitations on the total quantity of dispersant emitting substance which can be placed within the dispersant delivery systems without causing extreme reactions to the initial chemical release. Third, an inconsistent dispersant release rate is wasteful and leads to premature disposal of the dispersant delivery system. Fourth, with the volatilization of various components at different rates, the original fragrance "note" can be readily lost or distorted.

Another serious problem in developing a successful dispersant delivery system is that certain harsh dispersants tend to attack some materials which might otherwise be effective at providing a uniform chemical delivery rate. Accordingly, chemical resistance remains a major concern in the development of any dispersant system.

In recognition of some of these problems, a number of partial solutions have been suggested. In U.S. Pat. No. 3,790,081 issued Feb. 5, 1974, to Thornton et al. a manually adjustable device is provided for delivering chemicals to surrounding atmosphere. This device contains adjustable openings which can be proportioned to increase or decrease the amount of dispersion of vapors from the device. While this device does permit adjustment of the amount of flow, it requires regular monitoring and manipulation in order to achieve a constant rate of chemical dispersion. Additionally, for many applications this device is considered too complicated and bulky to allow it to be economically and conveniently employed.

A compact, self-regulating device is disclosed in U.S. Pat. No. 4,413,779 issued Nov. 8, 1983, to Santini. This device employs a simple container with a wick and porous plastic cap element from which evaporation occurs. In order to regulate the rate of dispersion, an occluding agent (e.g. isoparaffinic and normal paraffinic solvent) is impregnated into the porous plastic element to control the rate of dispersion. While this device may experience improved control of the rate of dispersion emission, more regular and better controlled dispersion is believed possible. Moreover, the use of paraffin is believed to seriously limit the chemical resistance of this device. Additionally, a still more compact and durable receptacle for the delivery of dispersant is likewise desired.

Another approach is shown in U.S. Pat. No. 4,917,301 issued Apr. 17, 1990, to Munteanu. In this device a container of liquid volatile substance is provided with an opening covered with a microporous membrane such as a non-woven polyester sheet. While this device may provide somewhat improved transfer of dispersant and may experience decreased contaminant build-up, a more consistent and linear rate of dispersion of dispersant continues to be sought. Another problem with this system is that it is limited in its chemical compatibility and may not be suitable for certain dispersants, such as very strong oils.

Another approach is taken in Japanese Laid-Open Patent Application JP 4-132556, laid open May 6, 1992. This patent is directed to a deodorizing bag filled with deodorant gel, sol or liquid and constructed from an air permeable and water impermeable material, such as polyethylene porous film, tetrafluoroethylene resin porous film, polyethylene terephthalate nonwoven cloth, or nylon nonwoven cloth. The deodorizing bags are durable and of minimal size, which allows them to be freely used in a wide variety of applications. Unfortunately, based upon the materials used in these bags they would be expected to suffer from the same inconsistent dispersion performance over time as the apparatus previously discussed.

Accordingly, it is a primary purpose of the present invention to provide a dispersant delivery apparatus and method which automatically delivers a relatively consistent level of chemical dispersant over the life of the apparatus.

It is a further purpose of the present invention to provide such an apparatus and method which can be formed of minimal size and complexity so as to provide dispersant delivery to many different applications.

It is another purpose of the present invention to provide an apparatus and method for dispersant delivery which employs a durable casing and transfer membrane so as to allow its use with a wide variety of dispersant materials and in many different environments.

These and other purposes of the present invention will become evident from review of the following specification.

SUMMARY OF THE INVENTION

The present invention is directed to an improved apparatus and method for the delivery of fragrances and other dispersants from a receptacle to surrounding atmosphere or other environment. The apparatus of the present invention comprises a sealed receptacle including a composite membrane of particular construction allowing it safely to contain volatile dispersant emitting substances in solid or liquid form while permitting the uniform dissipation of gaseous or suspended dispersant to the surrounding environment.

The preferred composite laminate of the present invention comprises a backing material, such as polymeric nonwoven, a permeable membrane such as expanded polytetrafluoroethylene film, and a coating such as a polytetrafluoroethylene resin. When combined in various forms in the manner disclosed, these elements produce a composite which resists wetting by low surface tension liquids and provides a regular and uniform surface for the release of a wide variety of dispersant materials The apparatus of the present invention is effective at delivering dispersant at an essentially linear rate over an extended period of time. The apparatus may be fashioned into any number of forms, shapes and sizes for different applications, including a plastic receptacle including an opening sealed with the composite or a durable sealed packet or pouch constructed partially or entirely from the composite.

The apparatus of the present invention can be employed to deliver a wide variety of dispersants, including fragrances, biologically active ingredients, humidifying or desiccating substances, chemically active ingredients, etc.

DESCRIPTION OF THE DRAWINGS

The operation of the present invention should become apparent from the following description when considered in conjunction with the accompanying drawings, in which:

FIG. 4 is a graph illustrating the relative performance over time of a dispersant delivery apparatus of the present invention verses previously available dispersant delivery apparatus.

DETAILED DESCRIPTION OF THE INVENTION

The present invention is a dispersant delivery apparatus and method for use in a variety of environments.

Figure 1:
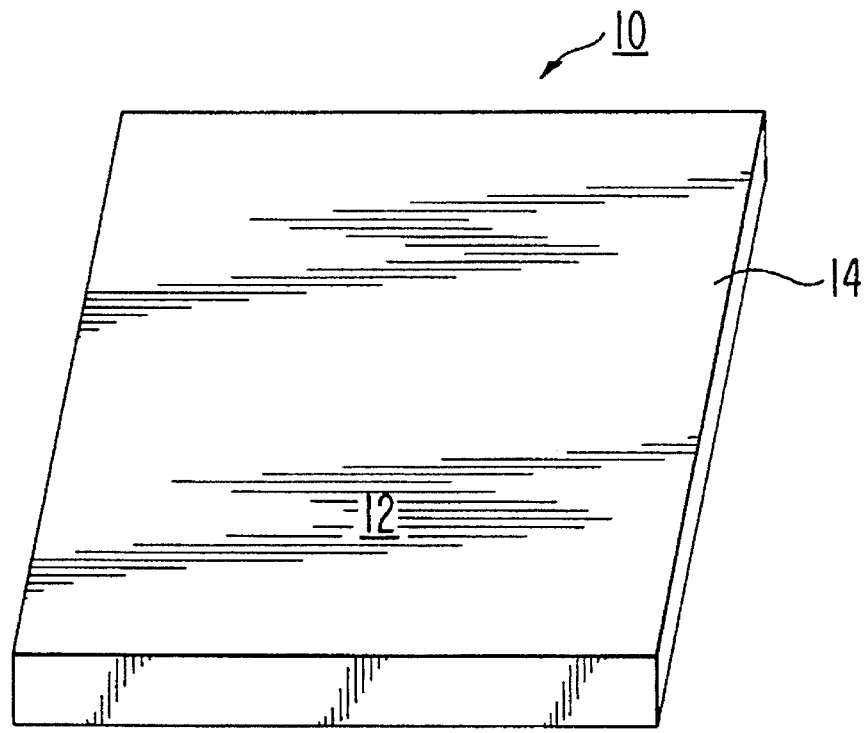
FIG. 1 is a three-quarter elevational isometric view of dispersant delivery packet of the present invention.

FIG. 1 illustrates one embodiment of a dispersant delivery apparatus 10 of the present invention. In this form the apparatus 10 comprises a receptacle in the form of a sealed packet 12 formed from a composite material. The packet 12 may be formed from multiple sheets of composite material 14 or may comprise a single sheet of material folded upon itself and sealed around its edges. In either instance, sealed within the packet is a dispersant emitting substance.

As used herein the term "dispersant" is intended to encompass any material which is being released into a surrounding environment, whether as a vapor, fine droplets, particles, or otherwise. The term "receptacle" is intended to include any container used to hold dispersant emitting substances.

Figure 2:
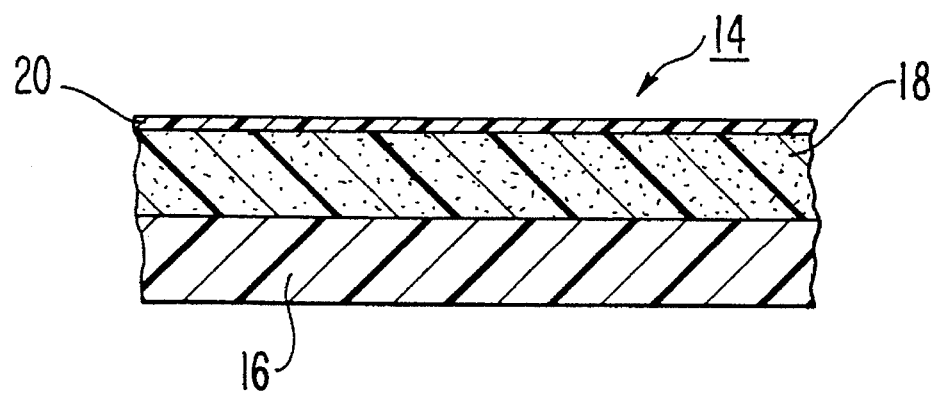
FIG. 2 is a cross-sectional view of a membrane and backing material laminate used in the present invention.

The composite material 14 of the present invention is shown in FIG. 2. The material 14 comprises a backing material 16, a permeable membrane 18, and a polymer coating 20. The unique properties of the composite material is imparted by the combination of a permeable membrane 18 with selected properties and the polymer coating 20 applied on the membrane 18.

The preferred permeable membrane 18 comprises a porous or permeable polymeric layer, for example a polyolefin and particularly a fluoropolymer such as polytetrafluoroethylene (PTFE), co-polymers of PTFE and/or other fluoropolymers, perfluorodioxole polymer, etc. Ideally the membrane comprises a membrane of PTFE which has been expanded to form a permeable network of polymeric nodes and fibrils. This material can be made in any known manner, such as in the manner disclosed in U.S. Pat. No. 3,953,566 issued Apr. 27, 1976, to Gore. As is known, this material has the unique ability of being water proof and moisture vapor permeable. As such, it has been determined that dispersant will freely dissipate through this membrane while dispersant emitting substance will be safely contained within the apparatus 10.

Expanded PTFE material is commercially available from W. L. Gore & Associates, Inc., Elkton, Md., in a variety of forms under the trademark GORE-TEX or ZINTEX. For use with most dispersant emitting substances, a preferred expanded PTFE membrane has the following properties: a nominal porosity of 30 to 70%; a nominal thickness of 3 to 4 mils; and a nominal bubble point of about 18 to >50 psi. The following are examples of preferred materials available from W. L. Gore & Associates, Inc., P.O. Box 1550, Elkton, Md., under the trademark GORE-TEX with the following properties and part numbers: 70% nominal porosity, 3 mils nominal thickness, and 18 psi nominal bubble point (Part No. XZ16735)(identified herein as "Sample A"); 50% nominal porosity, 4 mils nominal thickness, and >50 psi nominal bubble point (Part No. XZ16736)(identified herein as "Sample B"); and 30% nominal porosity, 4 mils nominal thickness, and >50 psi nominal bubble point (Part No. XZ16737)(identified herein as "Sample C").

Each of these properties are determined in the following manner: "Bubble point" is the pressure of air required to blow the first continuous bubbles detectable by their rise through a layer of isopropyl alcohol covering the PTFE media. The bubble point of the porous PTFE is measured using isopropyl alcohol following ASTM Test Method F316-86.

"Thickness" of porous PTFE is measured simply by using a snap gauge, such as a Mitutoyo Snap Gauge Model 7326 or Series 7, available from MTI Corporation of Paramus, N.J.

"Porosity" was determined by using the following equation:

$$\text{Porosity} = \left( \frac{p^{PTFE\ Bulk} - p^{PTFE\ Membrane}}{p^{PTFE\ Bulk}} \right) \times 100$$

Where P=density. Density was determined by standard mass and volume measurements on a 5"×5" sample. The accepted value for the standard density of solid bulk PTFE is 2.2 g/cc. Porosity is therefore the percentage void volume of PTFE membranes.

Figure 3:
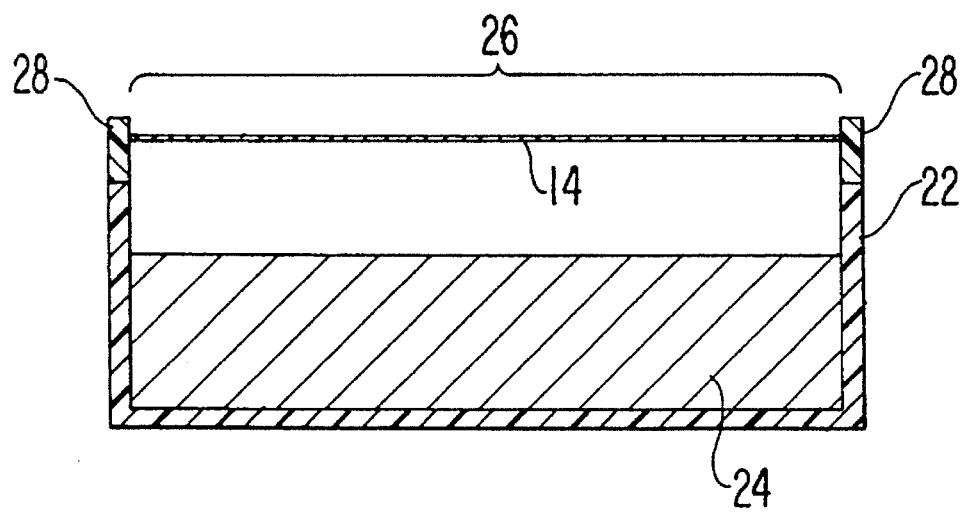
FIG. 3 is a cross-sectional view of another embodiment of a dispersant delivery apparatus of the present invention incorporating a receptacle with an opening sealed with a membrane/backing material laminate of the present invention.

While the above described expanded PTFE membranes will perform well in separating dispersant from most dispersant emitting substances, certain dispersants, especially certain liquids with a low surface tension, will have a tendency to permeate an untreated expanded PTFE membrane. This can eventually lead to leakage from the apparatus 10. Additionally, although flow across such membranes is well controlled, there remains a tendency for more volatile substances to permeate through the membrane more rapidly, leading to a somewhat inconsistent dispersion rate.

To address these concerns, a polymer coating 20 is applied to the membrane 18 of the present invention to provide further control of the permeability and leak resistance of the membrane. This coating should supply the following properties: low surface free energy (e.g., about 16 dyn/cm or less); chemical resistance; temperature resistance (e.g., about −5° up to 155° C.). The preferred coating 20 comprises a layer of PTFE and perfluorodioxole with a surface energy of less than about 16 dyn/cm. One commercial source for this material is E. I. dupont de Nemours and Company of Wilmington, Del., under the tradename TEFLON AF 1600.

The coating 20 can be applied to the membrane through any conventional manner, such as through spraying, dip coating, transfer coating, knife over roll, roller, etc. Preferably a 0.01 to 5% by weight solution is formed with a perfluorocarbon compound liquid, such as that available from Minnesota Mining & Manufacturing Co. under the designation PF5070, and the solution is sprayed onto the membrane. Coating is preferably performed with a add-on weight of 2% or less of TEFLON AF 1600 polymer. One method of coating believed suitable for use in the present invention is that set forth in U.S. Pat. No. 5,116,650 issued May 26, 1992, to Bowser.

It has been found that the combination of the expanded PTFE membrane 18 and the polymer coating 20 serves to provide mechanism for even and relatively consistent flow of dispersant chemical across the membrane while assuring safe containment of the dispersant emitting substances within the apparatus.

The use of the backing material 16 serves to protect and reinforce the membrane from distortion or damage. Additionally, the backing material 16 provides a layer to facilitate sealing to thermoplastic containers. Suitable materials for use in this regard should be porous, flexible and smooth, and include nonwoven and woven backing made from thermoplastic polymers, such as polyamides, polyester, polyvinyl chloride (PVC), polyethylene, polypropylene, poly(ethylene terephthalate) (PET), polytetrafluoroethylene (PTFE), fluorinated ethylenepropylene (FEP), and perfluoroalkoxy polymer (PFA), etc. The preferred material comprises a TYPAR 3151 polypropylene nonwoven manufactured by Reemay, Inc. of Old Hickory, Tenn.

It should be noted that the backing material 16 may likewise be coated in the manner disclosed herein. When the material is formed in this manner, it has the additional flexibility of being able to be used in either direction and being able to be sealed on either side.

A laminate of the backing material 16 and the membrane 18 can be formed in any suitable manner. Preferably the lamination is done by applying heat through the membrane via a heated roller and then compressing the backing material 16 via a resilient roller. By heating the membrane in excess of the melting temperature of the backing and applying pressure, a small portion of the outer surface of the backing is melted and forced into the porous matrix of the membrane. When the laminate is formed in this manner, the coating 20 should be applied when the laminate has cooled. Once the coated composite material 14 has been formed, it can then be fashioned into any suitable form for use in the present invention.

The present invention may be employed with a variety of dispersant emitting substances. Such substances may comprise any suitable form which will release dispersant to surrounding atmosphere, including solid, gel, liquid, and in some cases a gas. These substances can perform a variety of functions, including: serving as a fragrance or perfume source; supplying a biologically active ingredient such as a pesticide, pest repellent, bait, aromatic medicines, etc.; providing humidifying or desiccating substances; delivering air-borne active chemicals, such as corrosion inhibitors; etc.

The present invention can be employed with a wide variety of dispersion producing substances. It is particularly adapted for use with volatile and highly volatile substances. Certain chemicals, such as acids, alkalies, alcohols, ketones, petroleum distillates, aromatic hydrocarbons, and surfactants, can attack certain diffusion membranes and containers, leading to apparatus failure. The chemical resistance of the present invention can be freely employed with these chemicals without compromise of the apparatus. Additionally, other chemicals, such as oils and aliphatic hydrocarbons, have a low surface tension which can penetrate or leak through certain permeable membranes, including conventional expanded PTFE. The composite membrane of the present invention can be readily used with such materials with minimal risk of apparatus leakage. Moreover, with more even dispersion of chemical from the apparatus, fragrance essence or "note" can be maintained for a longer period of time.

The embodiment illustrated in FIG. 1 with the receptacle 12 in the form of a packet is ideal for instances where more complicated or bulky dispersion apparatus would not be appropriate. For example, the packet receptacle 12 can be constructed in various shapes and sizes to allow it to be inserted into a variety of environments, such as shoes, closets, compartments and containers, packages and luggage, cabinets, stationary and mobile heating, ventilating and air conditioning (HVAC) systems, refrigeration systems, etc. The receptacle can be made from mixed materials, some permeable and some impermeable, or it can be made entirely from permeable composite 14 to fine-tune the amount of dispersion. The use of durable fabric material has additional benefits of being break-resistant and readily disposable. This allows the receptacle 12 to be used in applications where it may be difficult or impossible to retrieve it, such as in underground gas storage tanks, bilge water systems, inaccessible spaces in industry or homes, etc.

Another embodiment of the present invention is shown in FIG. 3. In this embodiment a non-permeable receptacle 22 is employed to hold the dispersant emitting substance 24. The non-permeable portion of the receptacle 22 can be formed from any appropriate material, including polyester, polypropylene, perfluoroalkoxy polymer (PFA), fluoroethylene propylene (FEP), ethylene-chlorotrifluoroethylene (ECTFE), HALAR, poly(ethylene terephthalate) (PET), and polyvinylchloride (PVC). To permit and control the dissipation of dispersant from the receptacle 22, a composite membrane 14 of the present invention is sealed across an opening 26 in the receptacle 22. The composite 14 may be attached to a permanent or removable lid 28, as shown, or may be simply stretched across the opening 26 and held in place with a clamp, band, or similar device.

The embodiment shown in FIG. 3 has a number of desirable properties. First, when provided with a removable lid 28 or similar means of accessing the interior of the receptacle 22, the apparatus can be readily supplied with a fresh or different supply of dispersant emitting substances 24. Second, this embodiment is believed to be better adapted for use on countertops and in other applications where a decorated receptacle and/or some form of receptacle-attached mounting means may be desired. Third, this embodiment also lends itself to the inclusion of devices which can improve the operation of the apparatus. For example, a sealable or adjustable cap could be provided to allow the flow of dispersant from the receptacle to be ceased and/or modified, or an electric fan or similar circulation device may be included to improve flow from the apparatus. Fourth, this embodiment has a further capacity for holding larger quantities of dispersion producing substance 24 than a packet.

As was mentioned, the amount of flow of dispersant from the apparatus can be modified in a number of ways. First, the permeability of the membrane 14 itself can be modified by providing it with differing degrees of porosity or by applying to it different, or different amounts of, coating material. Second, the amount of membrane material which is used in the apparatus likewise will adjust the rate of flow from the apparatus. For instance, the apparatus may comprise different amounts of permeable and impermeable material. Similarly, more than one opening can be provided in the apparatus, each covered with composite membrane, to control the amount of flow from the receptacle. Third, means can be provided to seal part or all of the apparatus to prevent the dissipation of dispersant, either by sealing the apparatus in a wrapping, case or other container, or by providing a cap or similar seal over the composite membrane 14.

Shown in FIG. 4 is a graph illustrating the various performance curves which can be achieved with the present invention. Lines 30a, 30b, 30c each represent the weight loss performance of the three membranes previously identified as Sample A, Sample B, and Sample C, respectively.

The relative permeation rates of fragrance by Samples A, B, and C were determined as follows. About 2 grams of a fragrance (No. 31176) obtained from International Flavors and Fragrance (IFF) was placed into four round aluminum dishes (44 mm inside diameter (I.D.)×12 mm height). Each of the samples were then securely fastened over the lip of the dish using a rubber band to create a seal. The final pan was left without a membrane cover to serve as a control. Each pan was then weighed to establish an initial weight. The pans were stored at a temperature between 22° and 23° C. and a relative humidity of 30 to 50%. Each of the pans were then weighed intermittently over a 36 day period. The relative weight loss was determined by comparison to the initial weight. Any weight loss that occurred was assumed to be a result of fragrance vapor permeation through the membrane into the surrounding air. The results of this experiment are illustrated in FIG. 4.

As can be seen in FIG. 4, in each of these instances the present invention provides an even discharge of fragrance over its operative life. This discharge can be adjusted to range from that of line 30a, resembling an open air evaporation rate 32, to a relatively low level discharge represented by line 30c. By contrast, line 34 represents the inconsistent rate of discharge delivered from a conventional expanded PTFE membrane coated with a hydrophobic layer of polyurethane.

Figure 5:
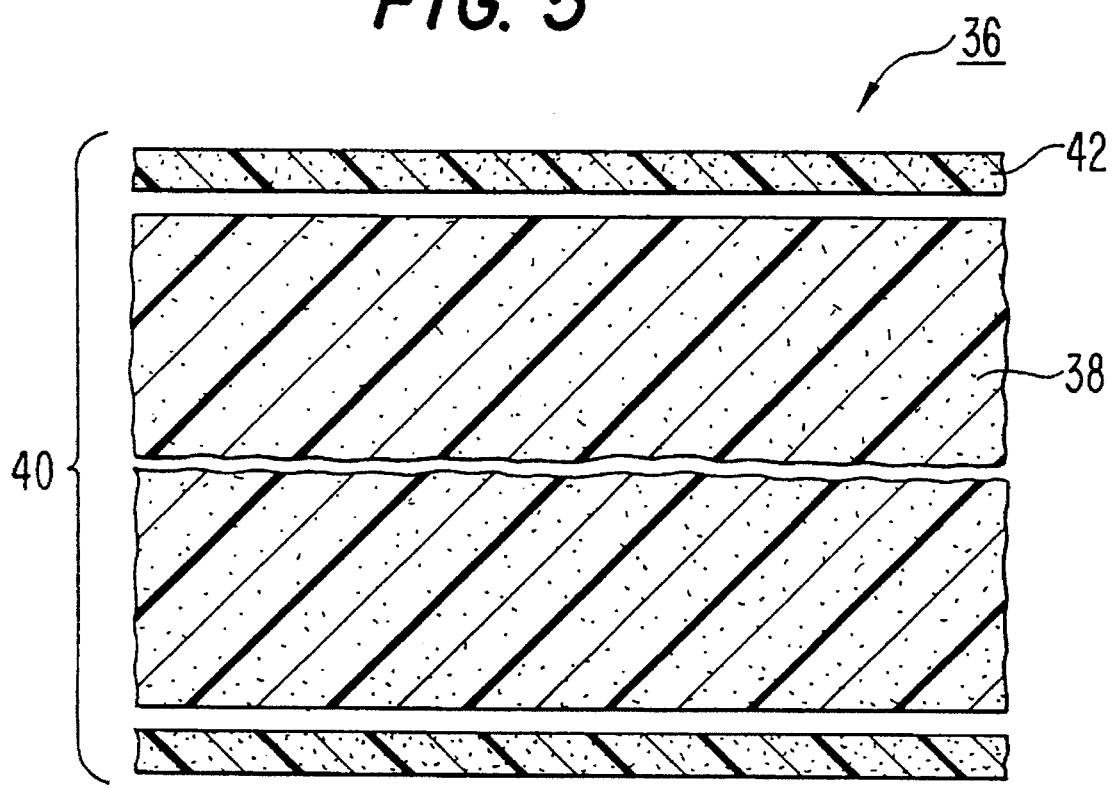
FIG. 5 is a cross-sectional view of yet another embodiment of the present invention, including an internal porous mass, which mass is shown truncated.

Yet another embodiment of the present invention is shown in FIG. 5. In this embodiment the apparatus 36 includes an interior porous mass 38 which is filled with dispersant emitting substance. The mass 38 is contained within a receptacle 40 including a permeable laminate composite 42 of the present invention. Ideally the mass 38 comprises an expanded PTFE, such as a joint sealant, tubing, etc. One suitable material comprises the expanded PTFE tube material employed in U.S. Pat. No. 5,235,863 issued Aug. 17, 1993, to Bailey et al., incorporated herein by reference.

Among the advantages of this embodiment is that the porous mass 38 provides a resilient substrate which will withstand compressive forces applied against the apparatus 36. This allows the apparatus, particularly in the form of a pouch or packet 14, to be far more durable and permits its application in instances where the apparatus may be placed under pressure. The use of a mass 38 also provides another means to delay dissipation of dispersant, prolonging the useful life of the apparatus.

Without intending to limit the present invention, the following represent examples of how the apparatus of the present invention can be made and used:

EXAMPLE 1

A dispersant delivery apparatus of the present invention was constructed in the following manner. A GORE-TEX expanded PTFE membrane was acquired from W. L. Gore & Associates, Inc. This membrane has the following properties:

Porosity=50%

IPA Bubble Point=>50 psi

Thickness=4 mils

Oil Rating=0.

The "oil rating" was determined by the following procedure, essentially following American Associates of Textile Chemists and Colorists (AATCC) Test Method 118-1989 Oil Repellency: Hydrocarbon Resistance Test, incorporated by reference. This test detects the presence of fluorochemical finish, or other compounds capable of imparting a low energy surface, on a fabric by evaluating the fabric's resistance to wetting by a selected series of liquid hydrocarbons of different surface tensions. The following compounds with AATCC Oil Repellency Rating Numbers were used:

| AATCC Oil Repellency Rating No. | Liquid Composition |
| --- | --- |
| 3 | n-hexadecane |
| 4 | n-tetradecane |
| 5 | n-dodecane |
| 6 | n-decane |
| 7 | n-octane |
| 8 | n-heptane |

A fabric specimen was placed on a flat surface with its membrane side up. Beginning with test liquid No. 3 (i.e., n-hexadecane) a series of small drops (about 3/16" in diameter) of test liquid were placed across the specimen. The specimen was then inspected for wetting and/or wicking in each of three regions where test liquid was applied across the width of the fabric. Wetting of the membrane was evidenced by the normally white opaque surface becoming tranlucent to transparent and thereby appearing dark on a black table top. Wicking appears as wetting, but with the darkening of the membrane occurring outside the drop area of the membrane. The drops were observed for a period of 30 seconds from about a 45° angle at a distance of about 12 inches. This procedure was repeated with increasing AATCC test liquid numbers until wetting/wicking occurred. The oil rating number is the last number of liquid applied which failed to wet/wick the fabric. With an oil rating of 0, the above described membrane wetted immediately with the lowest test liquid employed.

The above described membrane was laminated to a TYPAR 3151 polypropylene nonwoven backing material acquired from Reemay, Inc. Lamination was performed by applying heat through the membrane via a heated metal roll and then compressing the backing material into the heated membrane against the metal roll via a resilient polymeric roll. The membrane was thereby heated to a temperature in excess of the melting temperature of the backing. Upon applying pressure, a small portion of the outer surface of the backing was melted and was forced into the porous membrane matrix. Upon cooling below the melt temperature, the membrane remained adhered to the backing.

The membrane side of the composite laminate was then coated with a TEFLON AF 1600 PTFE resin. This was accomplished by spraying a solution of 0.5% by weight TEFLON AF 1600 resin in a perfluorocarbon compound liquid, available from Minnesota Mining & Manufacturing Co. under the designation PF5070. The PF5070 liquid was then volatilized in an IR oven. After the laminate was coated, it had the following properties:

Thickness=13.8 mils

Oil Rating=3 to 5.

The resulting coated laminate composite was then fabricated into pouches by use of a heat seal mechanism. Two same size swatches of composite were made. The two pieces were then placed one on top of the other such that the membrane was facing out on both pieces. A hot wire was then brought to rest, with applied pressure, onto the membrane surface. Heat was transferred from the wire through the membrane to melt the backing material and thus form a hermetic seal. This procedure was repeated on three sides of the pouch.

It should be noted that the pouches can likewise be constructed with the membrane facing inward. The same technique is then used to melt the backing material such that it will flow under pressure and fill the porous PTFE membrane and effect a hermetic seal. Again, this procedure is performed on three sides of the material.

Once the open pouch is formed, the pouch may be filled with any appropriate fragrance or other dispersant emitting substance. Once filled, the pouch can be heat sealed or clamped on the fourth side.

As has been explained above, this same laminate composite may also be used to seal a thermoplastic or thermoresin receptacle, allowing choice of a variety of container shapes and sizes.

The filled fragrance pouch was determined to release fragrance with an essentially linear rate of fragrance release over a period of thirty (30) days with no observable change in fragrance strength or note/essence during this period. As used herein, the term "linear rate of fragrance release" is intended to comprise a uniform (i.e., steady) release of a dispersant over an extended period of time. Examples of such linear rates are illustrated in FIG. 4 by lines 30a, 30b, and 30c.

Further, it has been observed that the fragrance producing substance will not leak, penetrate, or chemically damage the pouch. Accordingly, receptacles formed in accordance with the present invention have the long sought property of high degree of chemical compatibility which will not significanly alter the note of the dispensed fragrance.

Without intending to limit the scope of the present invention to such theory, it is believed that the combination of properties of membrane porosity, membrane thickness, membrane pore size, and oleophobicity provide the improved characteristics of this device.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A method for delivering a dispersant to a surrounding environment which comprises:

providing a receptacle having an interior adapted to contain dispersant emitting substance;

providing as part of the receptacle a composite of a backing material and a permeable membrane, wherein the composite is in communication with both the interior of the receptacle and the surrounding environment, and wherein the permeable membrane is selectively permeable to the dispersant so as to deliver a relatively consistent flow of dispersant release from the receptacle;

treating the composite with a fluoropolymer solution to cause it to be resistant to wetting by low surface tension liquids;

filling the receptacle with dispersant emitting substance; and sealing the receptacle so that dispersant dissipates from the interior of the receptacle through the composite.

2. The method of claim 1 which further comprises providing a permeable membrane of polytetrafluoroethylene (PTFE) with a nominal porosity of at least 30% and a nominal bubble point of at least 18 psi.;

treating the composite with a polymer of polytetrafluoroethylene and perfluorodioxole to cause it to be resistant to wetting by low surface tension liquids.

3. The method of claim 1 which further comprises forming the receptacle entirely from the composite.

4. An apparatus for transfer of a dispersant to surrounding environment which comprises:

a membrane selectively permeable to the dispersant while being resistant to wetting by low surface tension liquids;

a receptacle containing dispersant emitting substance, wherein at least a portion of the receptacle is sealed with the membrane, retaining low surface tension liquids within the receptacle while permitting dispersant to diffuse from the receptacle through the membrane;

wherein the membrane is coated with a layer of fluoropolymer to render it resistant to wetting by low surface tension liquids; and wherein the permeability of the membrane is such that a relatively consistent flow of dispersant release from the receptacle is provided.

5. The apparatus of claim 4 wherein the membrane is laminated to a backing material to form a composite.

6. The apparatus of claim 5 wherein the entire receptacle is formed from the composite.

7. The apparatus of claim 1 wherein the membrane comprises a porous expanded polytetrafluoroethylene (PTFE); and wherein the membrane and coating combine to produce a composite with an oil rating of at least 3.

8. The apparatus of claim 4 wherein the receptacle includes an interior of a porous mass filled with dispersant emitting substance.

9. The apparatus of claim 8 wherein the porous mass comprises expanded polytetrafluoroethylene.

10. The apparatus of claim 4 wherein the membrane is resistant to degradation when placed in contact with dispersion emitting substances.

11. A dispersant delivery apparatus which comprises:

a receptacle holding a dispersant emitting substance, at least a portion of the receptacle comprising a permeable composite;

wherein the composite comprises a permeable membrane of polytetrafluoroethylene (PTFE), the composite coated with a fluoropolymer to make it resistant to wetting by low surface tension liquids; and wherein the membrane has a permeability such that a relatively consistent flow of dispersant release from the receptacle is provided.

12. The apparatus of claim 11 wherein the membrane comprises a porous film of PTFE with a nominal porosity of at least 30%.

13. The apparatus of claim 11 wherein the membrane comprises a film of expanded PTFE with a nominal porosity of at least 30% and a nominal bubble point of at least 18 psi.

14. The apparatus of claim 11 wherein the membrane comprises a sheet of expanded PTFE; and the polymer comprises a layer of polytetrafluoroethylene (PTFE) and perfluorodioxidole.

15. The apparatus of claim 11 wherein the membrane comprises a material resistant to chemical attack from the dispersant emitting substance.

16. The apparatus of claim 11 wherein the membrane is resistant to degradation when placed in contact with dispersion emitting substances.

17. An apparatus for transfer of a dispersant to surrounding environment which comprises:

a membrane selectively permeable to the dispersant while being resistant to wetting by low surface tension liquids;

a receptacle containing dispersant emitting substance, wherein at least a portion of the receptacle is sealed with the membrane, retaining low surface tension liquids within the receptacle while permitting dispersant to diffuse from the receptacle through the membrane;

wherein the membrane is coated with a layer of fluoropolymer including a polytetrafluoroethylene to render it resistant to wetting by low surface tension liquids; and wherein the permeability of the membrane is such that a relatively consistent flow of dispersant release from the receptacle is provided.

18. The apparatus of claim 17 wherein the entire receptacle is formed from the membrane.

19. The apparatus of claim 17 wherein the membrane is coated with a layer of polytetrafluoroethylene and perfluorodioxidole.

20. An apparatus for transfer of a dispersant to surrounding environment which comprises:

a dispersant emitting substance;

a receptacle containing the dispersant emitting substance, the receptacle formed entirely from a composite of a membrane and a backing material, the membrane being selectively permeable to the dispersant;

wherein the membrane comprises a polytetrafluoroethylene that is resistant to wetting by low surface tension liquids; and wherein the permeability of the membrane is such that a relatively consistent flow of dispersant release from the receptacle is provided.

21. The apparatus of claim 20 wherein the membrane is coated with a layer of fluoropolymer to render it more resistant to wetting by low surface tension liquids.

22. The apparatus of claim 21 wherein the fluoropolymer includes perfluorodioxidole.

* * * * *